(12) United States Patent
Kelly et al.

(10) Patent No.: US 10,595,763 B2
(45) Date of Patent: Mar. 24, 2020

(54) INTEGRATED TESTING DEVICES WITH CONTROL VESSEL FOR FLUID CONTROL

(71) Applicant: ATOMO DIAGNOSTICS PTY LIMITED, New South Wales (AU)

(72) Inventors: John Kelly, New South Wales (AU); Huw Wallis, New South Wales (AU); Gianluigi Bortoluzzi, New South Wales (AU)

( * ) Notice: Subject to any disclaimer, the term of this patent is extended or adjusted under 35 U.S.C. 154(b) by 583 days.

(21) Appl. No.: 15/038,365

(22) PCT Filed: Nov. 21, 2014

(86) PCT No.: PCT/IB2014/066219
§ 371 (c)(1),
(2) Date: May 20, 2016

(87) PCT Pub. No.: WO2015/075677
PCT Pub. Date: May 28, 2015

(65) Prior Publication Data
US 2016/0287155 A1    Oct. 6, 2016

(30) Foreign Application Priority Data

Nov. 21, 2013  (AU) .................................. 2013904512

(51) Int. Cl.
*G01N 33/543*  (2006.01)
*A61B 5/157*  (2006.01)
(Continued)

(52) U.S. Cl.
CPC .......... *A61B 5/157* (2013.01); *A61B 5/14514* (2013.01); *A61B 5/14532* (2013.01);
(Continued)

(58) Field of Classification Search
CPC ............ A61B 10/0038; A61B 10/0051; A61B 10/007; A61B 5/150022; A61B 5/150343;
(Continued)

(56) References Cited

U.S. PATENT DOCUMENTS

| | | | |
|---|---|---|---|
| 4,246,339 A * | 1/1981 | Cole ................... | B01L 3/50255 422/534 |
| 4,637,403 A | 1/1987 | Garcia et al. | |

(Continued)

FOREIGN PATENT DOCUMENTS

| | | |
|---|---|---|
| CN | 101641052 | 1/2013 |
| EP | 1284121 | 2/2003 |

(Continued)

OTHER PUBLICATIONS

International Search Report dated Dec. 20, 2011 in International Application No. PCT/AU2011/001321, International Filing Date Oct. 17, 2011. (4 pages).
(Continued)

*Primary Examiner* — Christopher L Chin
(74) *Attorney, Agent, or Firm* — Shutts & Bowen LLP (57) ABSTRACT

An integrated testing device is described, for example for testing bodily fluids. The device has a test component, a reservoir containing a test fluid, and a control vessel. The reservoir discharges test fluid into the control vessel, which discharges the test fluid in a controlled way to the test component.

12 Claims, 7 Drawing Sheets

(51) Int. Cl.
*A61B 5/15* (2006.01)
*B01L 3/00* (2006.01)
*A61B 5/151* (2006.01)
*G01N 33/53* (2006.01)
*A61B 5/145* (2006.01)
*A61B 10/00* (2006.01)

(52) U.S. Cl.
CPC .......... *A61B 5/14546* (2013.01); *A61B 5/151* (2013.01); *A61B 5/150022* (2013.01); *A61B 5/15113* (2013.01); *A61B 5/15117* (2013.01); *A61B 5/15144* (2013.01); *A61B 5/150343* (2013.01); *A61B 5/150358* (2013.01); *A61B 5/150412* (2013.01); *A61B 5/150503* (2013.01); *A61B 5/150618* (2013.01); *A61B 5/150717* (2013.01); *A61B 5/150755* (2013.01); *A61B 10/007* (2013.01); *A61B 10/0038* (2013.01); *A61B 10/0051* (2013.01); *B01L 3/502* (2013.01); *B01L 3/5023* (2013.01); *G01N 33/5302* (2013.01); *A61B 2010/008* (2013.01); *B01L 2200/0605* (2013.01); *B01L 2200/16* (2013.01); *B01L 2300/046* (2013.01); *B01L 2400/0481* (2013.01); *B01L 2400/0683* (2013.01)

(58) Field of Classification Search
CPC ........ A61B 5/150358; A61B 5/150412; A61B 5/150503; A61B 5/150618; A61B 5/150717; A61B 5/150755; A61B 5/15113; A61B 5/15117; A61B 5/15144; A61B 5/157; A61B 2010/008; A61B 5/14514; A61B 5/14532; A61B 5/14546; A61B 5/151; B01L 3/5023; B01L 2200/16; B01L 2400/0481; B01L 2400/0683; B01L 3/502; B01L 2200/0605; B01L 2300/046
USPC ....................................................... 435/288.5
See application file for complete search history.

(56) References Cited

U.S. PATENT DOCUMENTS

| | | | |
|---|---|---|---|
| 4,661,319 A | | 4/1987 | Lape |
| 4,857,453 A | * | 8/1989 | Ullman ............ G01N 33/54366 435/7.92 |
| 4,918,025 A | * | 4/1990 | Grenner ................ B01L 3/5027 422/565 |
| 4,943,522 A | * | 7/1990 | Eisinger ........... G01N 33/54386 422/537 |
| 4,981,786 A | * | 1/1991 | Dafforn .............. G01N 33/5302 422/412 |
| 5,096,669 A | | 3/1992 | Lauks et al. |
| 5,135,873 A | * | 8/1992 | Patel .................... B01L 3/5023 422/412 |
| 5,249,584 A | | 10/1993 | Karkar et al. |
| 5,503,985 A | * | 4/1996 | Cathey ................ B01F 13/0059 422/504 |
| 5,714,390 A | | 2/1998 | Hallowitz et al. |
| 6,264,619 B1 | | 7/2001 | Ferguson |
| 6,319,209 B1 | * | 11/2001 | Kriz .................... G01N 33/5302 600/583 |
| 6,830,551 B1 | | 12/2004 | Uchigaki et al. |
| 7,488,298 B2 | * | 2/2009 | Patel .................. A61B 5/14532 600/573 |
| 7,885,697 B2 | | 2/2011 | Brister et al. |
| 7,946,984 B2 | | 5/2011 | Brister et al. |
| 8,229,534 B2 | | 7/2012 | Brister et al. |
| 2002/0002344 A1 | | 1/2002 | Douglas et al. |
| 2002/0150501 A1 | | 10/2002 | Robertson et al. |
| 2003/0013121 A1 | | 1/2003 | Khan |
| 2003/0028125 A1 | * | 2/2003 | Yuzhakov .......... A61B 5/14514 600/583 |
| 2005/0283094 A1 | | 12/2005 | Thym et al. |
| 2006/0127886 A1 | | 6/2006 | Kaylor et al. |
| 2007/0100213 A1 | | 5/2007 | Dossas et al. |
| 2008/0319347 A1 | | 12/2008 | Keren |
| 2010/0036282 A1 | | 2/2010 | List et al. |
| 2010/0184126 A1 | | 7/2010 | Rutty et al. |
| 2011/0039261 A1 | | 2/2011 | Hillebrand et al. |
| 2011/0105951 A1 | | 5/2011 | Bernstein |
| 2011/0144465 A1 | | 6/2011 | Shults et al. |
| 2011/0190614 A1 | | 8/2011 | Brister et al. |
| 2012/0283543 A1 | | 11/2012 | Brauker et al. |
| 2013/0131479 A1 | | 5/2013 | Kelly et al. |
| 2013/0323123 A1 | | 12/2013 | Kelly et al. |

FOREIGN PATENT DOCUMENTS

| | | |
|---|---|---|
| EP | 1374770 | 1/2004 |
| JP | 2012505639 | 3/2012 |
| JP | 5127839 | 1/2013 |
| WO | 1988000812 | 2/1988 |
| WO | 2001013795 | 3/2001 |
| WO | 2002010754 | 2/2002 |
| WO | 2002078533 | 10/2002 |
| WO | 2004078232 | 9/2004 |
| WO | 2006037646 | 4/2006 |
| WO | 2007062728 | 6/2007 |
| WO | 2008056363 | 5/2008 |
| WO | 2008085052 | 7/2008 |
| WO | 2008149333 | 12/2008 |
| WO | 2009147680 | 12/2009 |
| WO | 2011113114 | 9/2011 |
| WO | 2012048388 | 4/2012 |

OTHER PUBLICATIONS

International Preliminary Report on Patentability dated Jul. 30, 2012 in International Application No. PCT/AU2011/000315, International Filing Date Mar. 18, 2011. (12 pages).
International Search Report dated Jun. 14, 2011 in International Application No. PCT/AU2011/000315, International Filing Date Mar. 18, 2011. (7 pages).
Supplementary Partial European Search Report dated Jan. 31, 2014 in EP Application No. 11 75 5574. (7 pages).
International Search Report dated Apr. 20, 2015 in International Application No. PCT/IB2014/066219, International Filing Date Nov. 21, 2014. (4 pages).

* cited by examiner

INTEGRATED TESTING DEVICES WITH CONTROL VESSEL FOR FLUID CONTROL

CROSS REFERENCE TO RELATED APPLICATIONS

This Non-provisional Application is a 35 USC Sect. 371 National Stage entry of PCT/IB2014/066219 entitled FLUID CONTROL IN INTEGRATED TESTING DEVICES, filed Nov. 21, 2014 which claims the benefit of Australian Application No. 2013904512 filed on Nov. 21, 2013, the entireties of which are incorporated herein by reference.

TECHNICAL FIELD

The present invention relates to devices and methods for providing tests relating to bodily fluids such as blood, and particularly to the devices which facilitate such testing.

BACKGROUND OF THE INVENTION

Systems for performing relatively immediate medical tests, assays or diagnoses with relative ease are known. These may be, for example, home tests, point of care, or used in pathology clinics or hospitals. However, performing these relatively tests can require complicated instructions and multiple devices. The following discussion is not concerned with the specific biochemical or chemical tests to be performed, but rather with the device and associated mechanical systems which house and contain the test strips or similar components. For example, such devices and systems may be used with a lateral flow or other type of rapid test.

In a typical conventional home or point of care blood test, for example, the user is presented with a collection of components, including the test device itself, a separate lancet, blood collection receptacles, a container of buffer or other test fluid, an adhesive bandage, cleaning wipes, and possibly further components. The user is expected to follow a very precise sequence of steps, typically including cleaning the site, operating the lancet, obtaining a blood sample of a known volume and delivering it to the precise place required, applying a buffer solution at the right time and place and in the correct volume, and reading the test result and interpreting it.

Many tests are performed either as infrequent or one off procedures, so that the user does not become proficient through regular use. Procedures performed at point of care are carried out generally by skilled operators, but again the complexity and dexterity required to carry out the test accurately presents a challenge and specific tests may be performed infrequently. In such situations it would be advantageous if the test device could better facilitate simple, reliable and accurate operation.

In PCT application numbers PCT/AU2011/000315 and PCT/AU2011/022321, the disclosures of which are incorporated by reference herein, the present applicant has disclosed integrated testing devices. In particular, those devices may include a reservoir or sachet of a physiologically acceptable fluid, such as a buffer. For many tests, for example certain blood tests, it is required that a buffer or other reagent is applied to the test material after the blood sample, in order to achieve a valid result or to achieve the result within an acceptable timeframe. The devices disclosed in embodiments of these disclosures permit the user to discharge a fluid, illustratively a buffer, from the internal reservoir onto the test material.

It is an object of the present invention to provide a test device and method which improves the delivery of buffer or other test fluids to a test material.

SUMMARY OF THE INVENTION

In a broad form, the present invention provides a test unit including a reservoir for buffer or other test fluid. The test fluid may be selectively released by the user. The test unit includes a vessel which can accept the fluid so discharged, and then release the fluid from the vessel in a controlled way in order to contact the test material.

According to one aspect, the present invention provides an integrated testing device comprising:
 a test component;
 a reservoir adapted to contain a test fluid;
 a control vessel; and
 a fluid delivery actuator, wherein operation of the fluid delivery actuator causes the test fluid to be released from the reservoir into the control vessel, the control vessel being adapted to provide a controlled discharge of test fluid onto the test component.

According to another aspect, the present invention provides a method of testing a bodily fluid, using a device which includes a test component, a reservoir adapted to contain a test fluid, a control vessel, and a fluid delivery actuator, the method including at least the steps of:
 placing a sample of the bodily fluid on the test component
 operating the fluid delivery actuator;
 releasing the fluid form the reservoir to the control vessel;
 the fluid being released from the control vessel onto the test material as a controlled discharge.

According to another aspect, the present invention testing device including a control vessel adapted to receive a test fluid, and a test component, the test fluid being released from a separate or integral reservoir into the control vessel, the control vessel being adapted to provide a controlled discharge of test fluid onto the test component. The test fluid may be discharged from an integrated reservoir into the control vessel, or manually dispensed into the vessel from a sachet, dropper or other container.

It has been recognised by the applicant that, in some instances, the relatively rapid and potentially uncontained release of fluid onto the test component may reduce the accuracy of the test, or even compromise it altogether. Fluid may be delivered too quickly, may not be delivered to the correct site, and/or may not have a proper relationship to the test sample. It will be appreciated that implementations of the present invention allow for a relatively rapid discharge from the fluid storage, for example a sachet, while allowing for a slower rate of release to the test material. The rate of release may not be constant, and may be provided simply by an orifice in the vessel. The vessel may be generally sealed, or could be open to the outside, for example similar to a bowl in form. It may be one or more tortuous paths, which act to slow or limit the flow rate of the fluid onto the test material. Some part of the flow could arrive directly at the test material, whilst one or more other paths arrive more slowly. The term 'control vessel' is intended to encompass any structures included in the test unit which have the effect of controlling the rate of flow from a reservoir onto the test material.

It is specifically noted that the present invention encompasses a test unit in which the sachet is not integral, but manually discharged into the control vessel. Such a control vessel can be of assistance even in such a simple device.

Implementations can also, allow for different rates of release, simply by varying the size and/or shape of the opening in the vessel. The fluid may be released directly from the control vessel onto the test component, or via a conduit or channel.

The term 'controlled discharge' throughout the description and claims refers to releasing the fluid from the vessel in a way which is more controlled in flow rate than simply releasing the full contents of the sachet in a single burst. It may, in one form, merely amount to slowing down the rate of flow. It may in other forms more closely control the rate of discharge and adapt it closely to the requirements of the test. In many forms, the discharge rate will not be constant.

BRIEF DESCRIPTION OF THE DRAWINGS

Illustrative embodiments of the present invention will now be described with reference to the accompanying drawings, in which.

DETAILED DESCRIPTION OF THE INVENTION

The present invention will be described with reference to a number of possible embodiments. It will be appreciated that the present invention is capable of being implemented in numerous ways, in addition to the examples provided. The embodiments are intended as illustrative, and are in no way limitative of the inventive concept or its possible implementations. Further, it will be understood that the features of different embodiments may be formed into different combinations, or added together, in order to provide further implementations of the present invention.

The present invention is principally concerned with a specific aspect of the operation of a test device, relating to the discharge of a fluid which is intended to contact the test material. Accordingly, while specific examples of the remaining mechanical structures of a test unit will be provided and described, it will be understood that in principle the present invention can be used with any design of such a test unit. In particular, known test units, as well as those disclosed in the specifications incorporated by reference, may be modified so as to incorporate implementations of the present invention.

Figure 1:
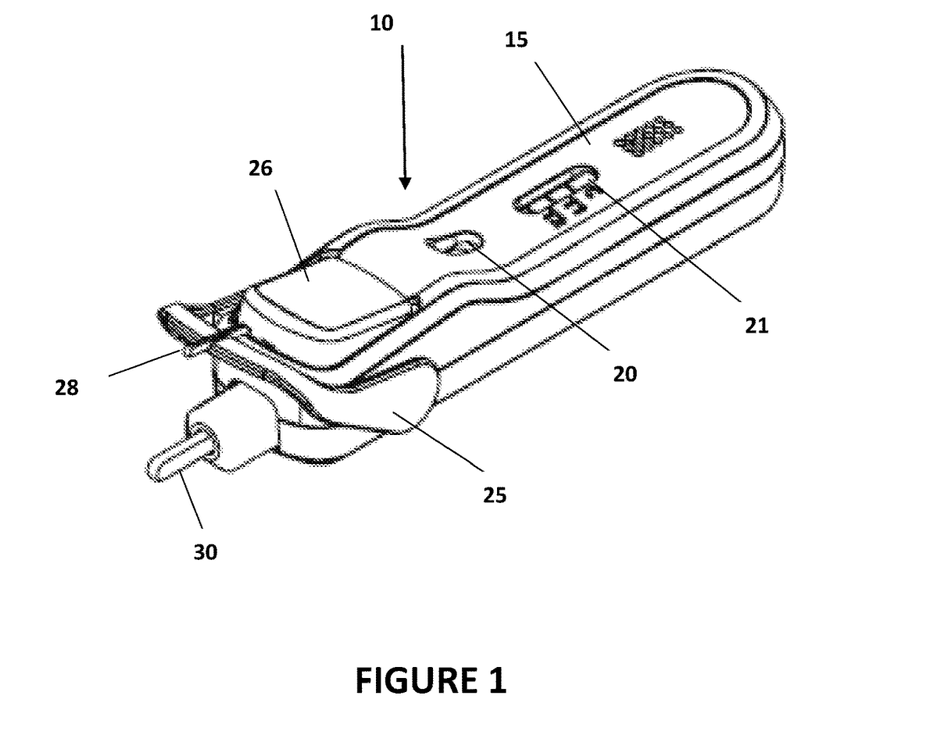
FIG. 1 shows a perspective view of one implementation of the present invention.
Figure 2:
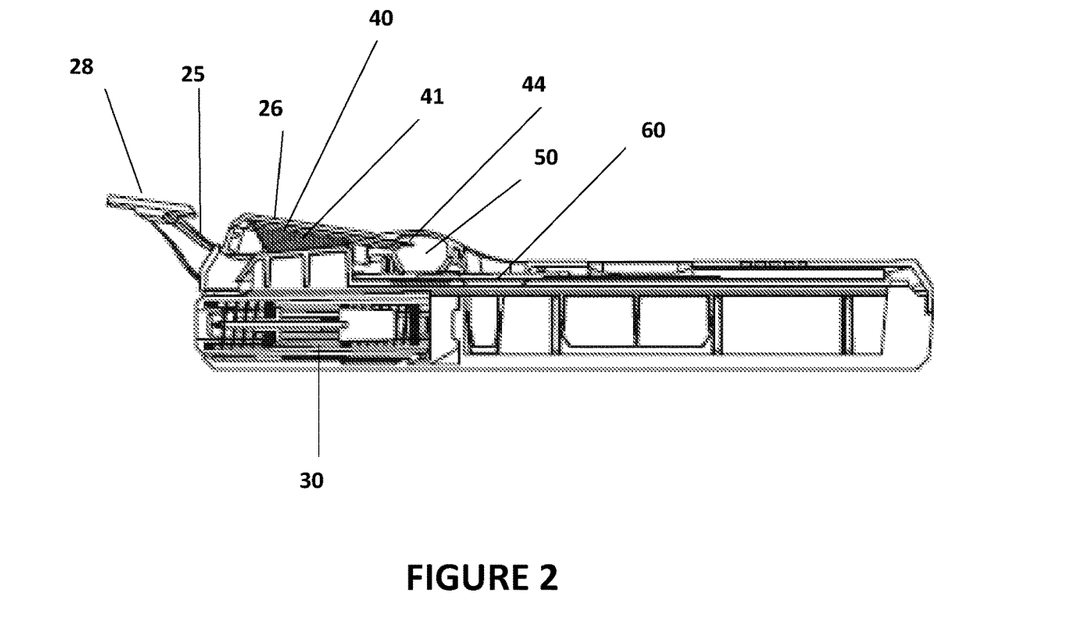
FIG. 2 is a longitudinal cross section a view of the implementation of FIG. 1.

FIGS. 1 and 2 illustrate one implementation of the present invention, in cross section in FIG. 2. The test unit 10 includes a cover 15, which includes a depressible section 26 for releasing the test fluid. The test fluid 41 is contained in a sachet 40. Test unit 10 further includes an arm 25 with a collection device 28 for a bodily fluid, in this case blood.

Test unit 10 also has an opening 20 for a blood sample to be received, and an indicator opening 21, through which the result of the test can be seen.

As will be described in more detail below, in use, the operator according to this embodiment operates lancet 30 to release blood from a suitable site on the body, for example a finger. In this implementation lancet 30 is integrated with the unit, although in other implementations it could be a separately supplied device. The user may need to milk the blood from the lanced site.

Collection device 28 is placed onto the exuded blood, and withdraws (in this case by capillary action) a sample. Other sample collection arrangements may be used in alternative implementations, for example a non-integral suction or capillary device, or direct placement of the fluid onto the test material 60.

After the collecting device is filled, the arm 25 may then be rotated (as will be described in more detail below) into a delivery position. The collection device is then in contact, via opening 20, with test material 60, and the sample is discharged onto test material 60.

The user may then depress section 26, which applies pressure to sachet 40 so that the test fluid 41 is released. Test fluid 41 flows into vessel 50. Vessel 50 has one or more openings (not shown in these views) which allow test fluid 41 to discharge at a controlled rate onto test material 60.

It is emphasised that the present invention can be applied to any kind of test, where the rate of test fluid needs to be controlled. In this case, the test is illustratively a lateral flow test. However, any other desired type of chromatographic or other test may be used. Similarly, the test fluid may be water, a buffer solution, or any other required fluid to conduct, support or be otherwise used in conjunction with the test.

Figure 6A:
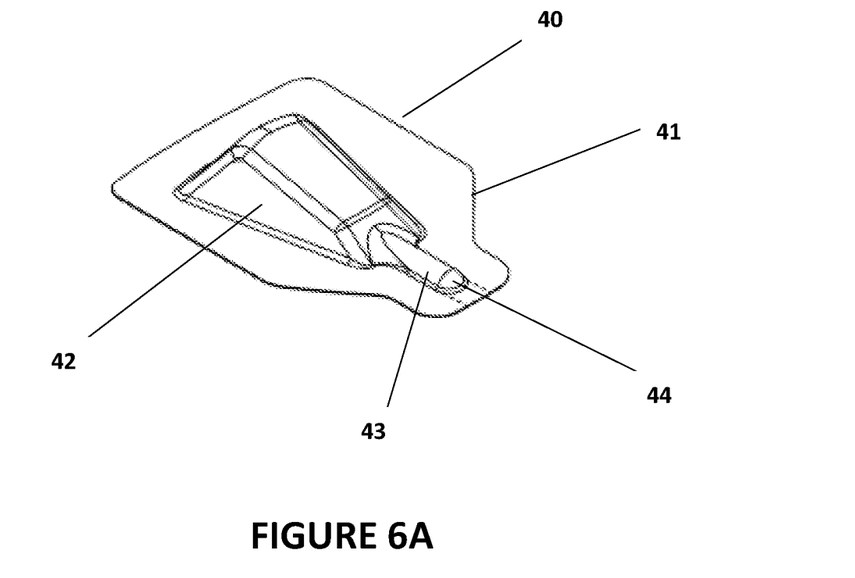
FIGS. 6A and 6B are perspective views of one implementation of a fluid reservoir.
Figure 6B:
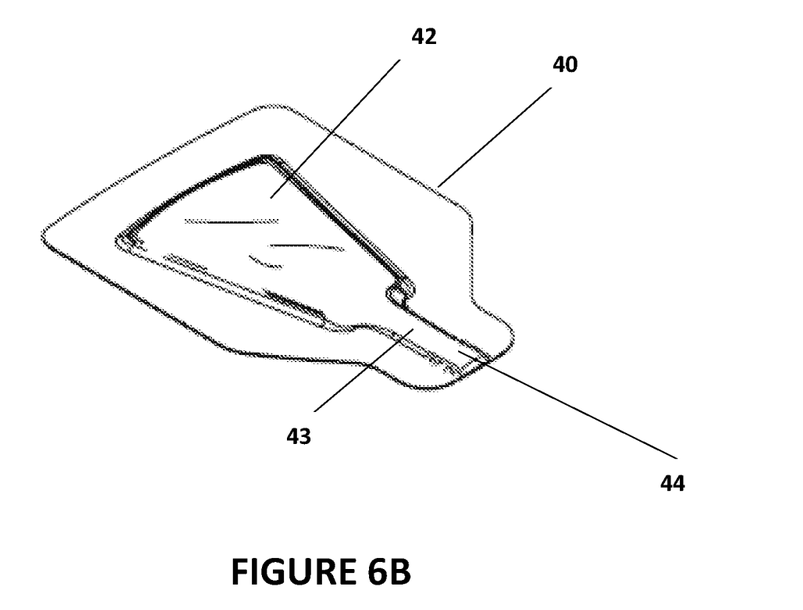

FIGS. 6A and 6B illustrate one implementation of the sachet 40, in this case as a structure formed in a similar way to a blister pack. Fluid is contained in the blister section 42. An outlet tube 43 is closed by a seal 44 with a reduced strength relative to the rest of the device, for example by having a thinner wall. Such a sachet may be manufactured using conventional blister pack technology.

When force is applied by depressible section 26, the pressure in the blister increases, until the seal 44 fails, and the fluid id discharged through tube 43. In FIG. 6B, it can be seen that blister 42 is depressed, all the fluid is discharged, through the now open tube 43.

Figure 3:
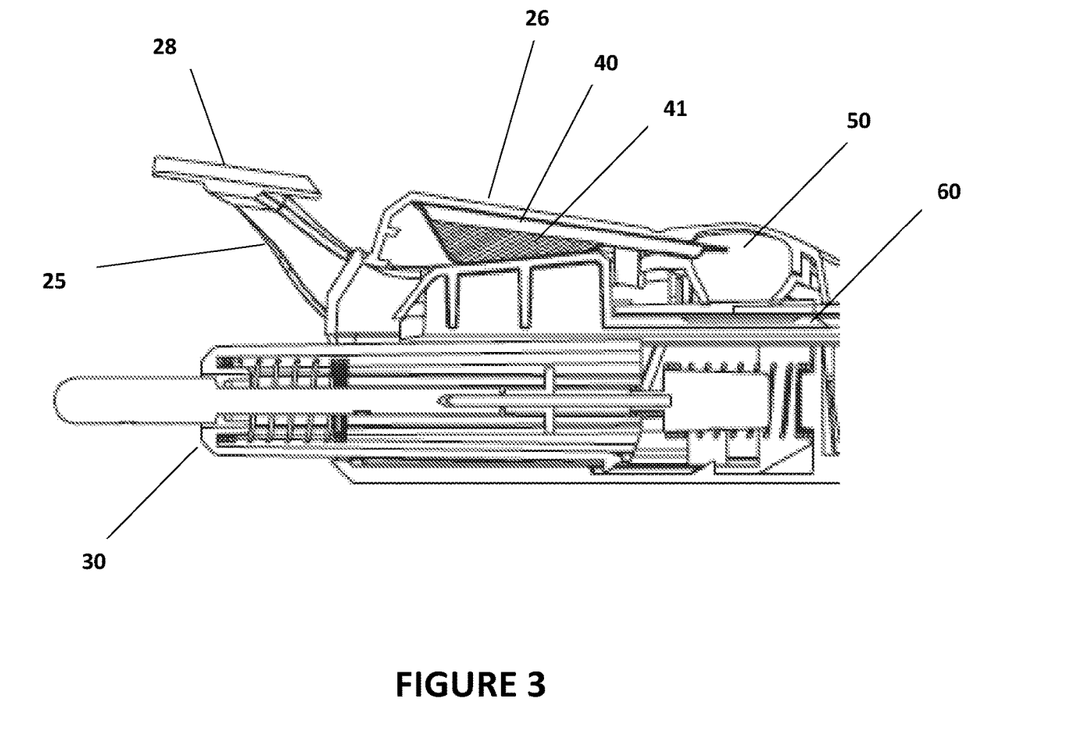
FIG. 3 is a more detailed cross sectional view.
Figure 5:
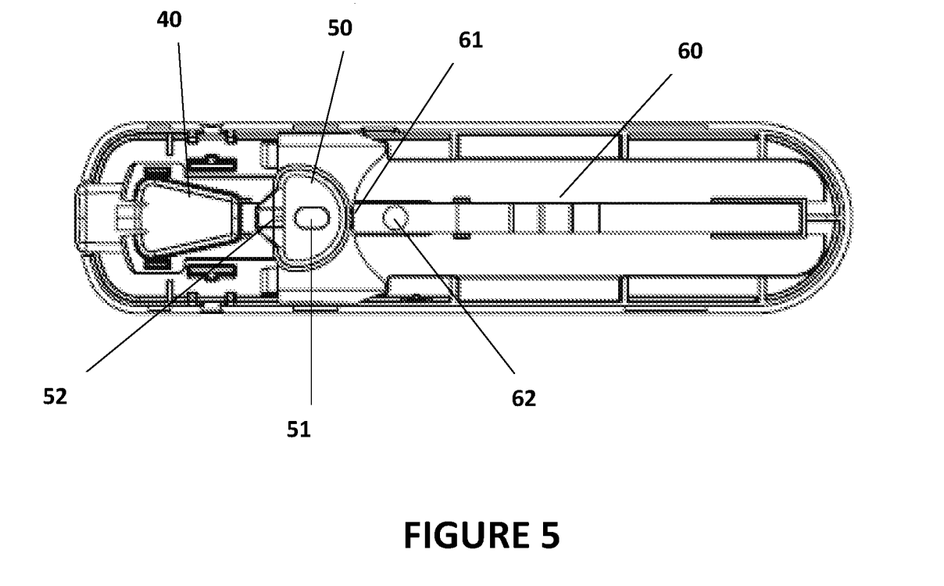
FIG. 5 is a plan view, with the cover removed, of the implementation of FIG. 1.

The operation of the overall system, and its discharge, can be better understood from FIGS. 3 and 5. In FIG. 3, the sachet 40 with test fluid 41 can be seen, under the depressible portion 26. The arm 25 which carried the collection device 28 can also be seen. When the fluid discharges from the sachet 40, it is collected in vessel 50, via discharge conduit 52. Vessel 50 has an opening 51 in its bottom wall, which discharges directly onto area 61 of the test material 60. Region 62 marks the point where the bodily fluid would be deposited via opening 20, and so it can be seen that the discharged test fluid is deposited so as to allow the test fluid to meet the sample after it is deposited.

It will be understood that the sachet or reservoir may be provided using any suitable technology, preferably including a referred failure direction for discharge under pressure. However, it will be appreciated that other release mechanisms, for example cutting or puncturing, could be used to release the fluid.

Figure 4A:
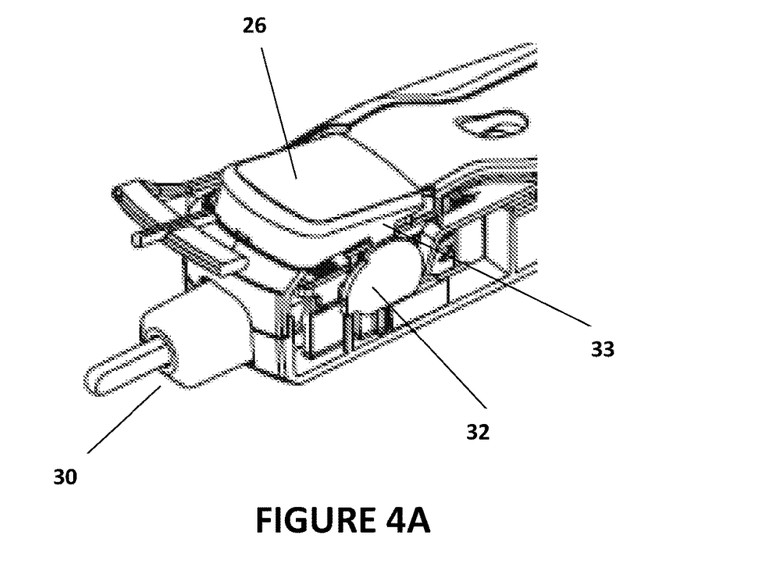
FIGS. 4A, 4B and 4C illustrate the operation of an interlock component in the implementation of FIG. 1.
Figure 4B:
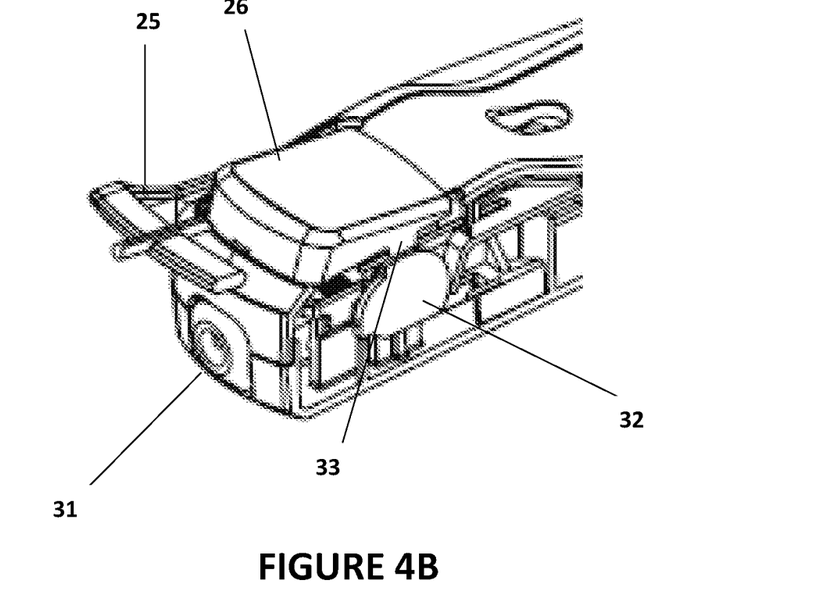
Figure 4C:
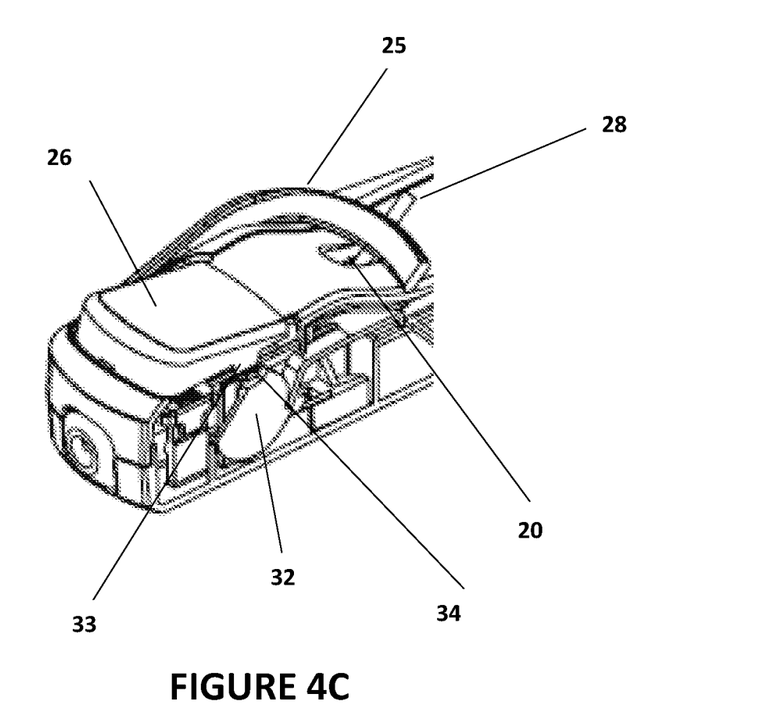

FIGS. 4A, 4B and 4C illustrate the operation of an interlock, which in a preferred implementation for a blood application ensures that the test fluid is only discharged onto the test material after the blood sample is deposited. In FIG.

4A, cam 32 can be seen. As will be explained in more detail, the rotational position of cam 32 determines whether the fluid in the reservoir can be released.

In FIG. 4A, the lancet 30 is in a rest position, and so no blood has yet been drawn. Projection 33 on depressible portion 26 is engaged by cam 32, and cannot move downwards. In FIG. 4B, the lancet has been engaged and operated, and has moved to a safe rest position 31. Blood can now be collected in collection device 28. Cam 32 still blocks projection 33.

In FIG. 4C, arm 25 has been rotated, so that blood can be deposited onto the test material 60 via opening 20. Cam 32 has now rotated so that recess 34 is located adjacent projection 33, and the depressible portion 26 can now be moved downward, so as to exert pressure on the sachet and release the fluid (not shown in this view). Thus, cam 32 acts as an interlock to prevent premature release of the test fluid. It will be appreciated that other mechanical system could be used to achieve this. Examples of such mechanisms are provided in the aforementioned patent applications. In many cases, the timing of the delivery of the fluid is critical to a proper result, and premature release will invalidate the test.

Figure 7A:
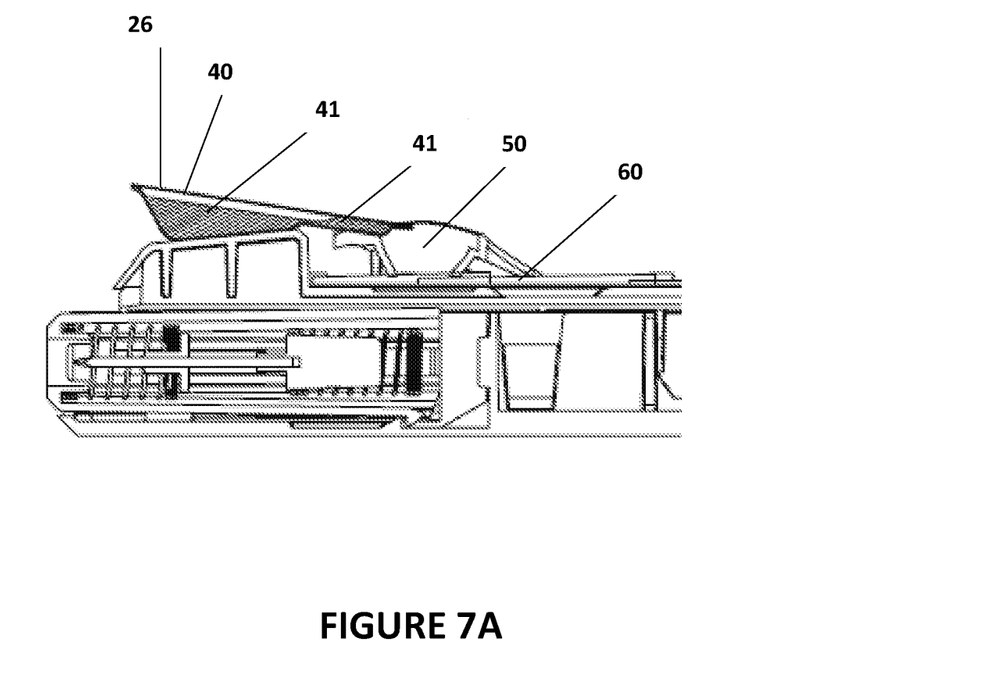
FIGS. 7A, 7B and 7C illustrate in cross section the stages in discharge of test fluid.
Figure 7B:
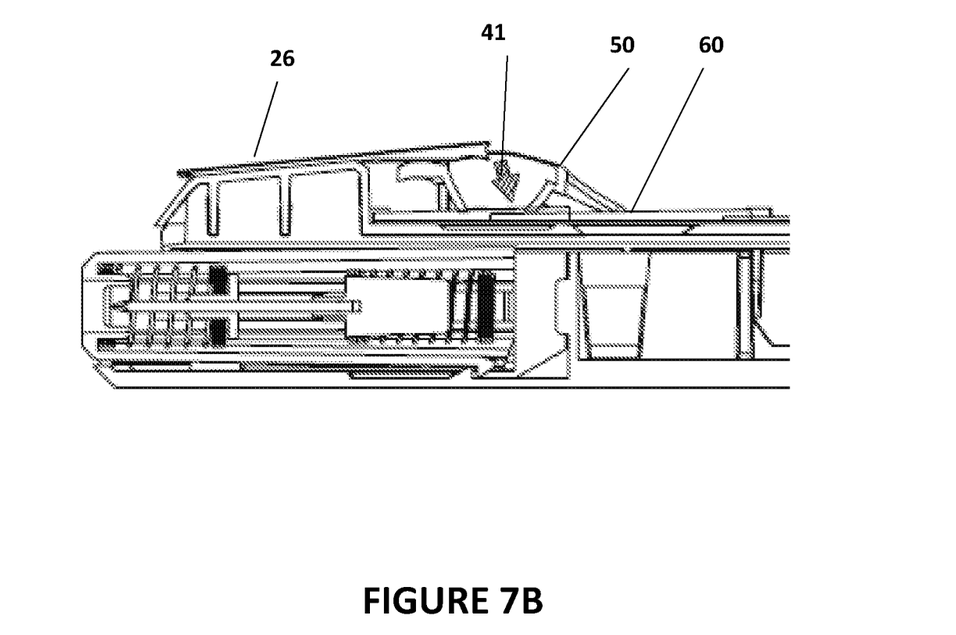
Figure 7C:
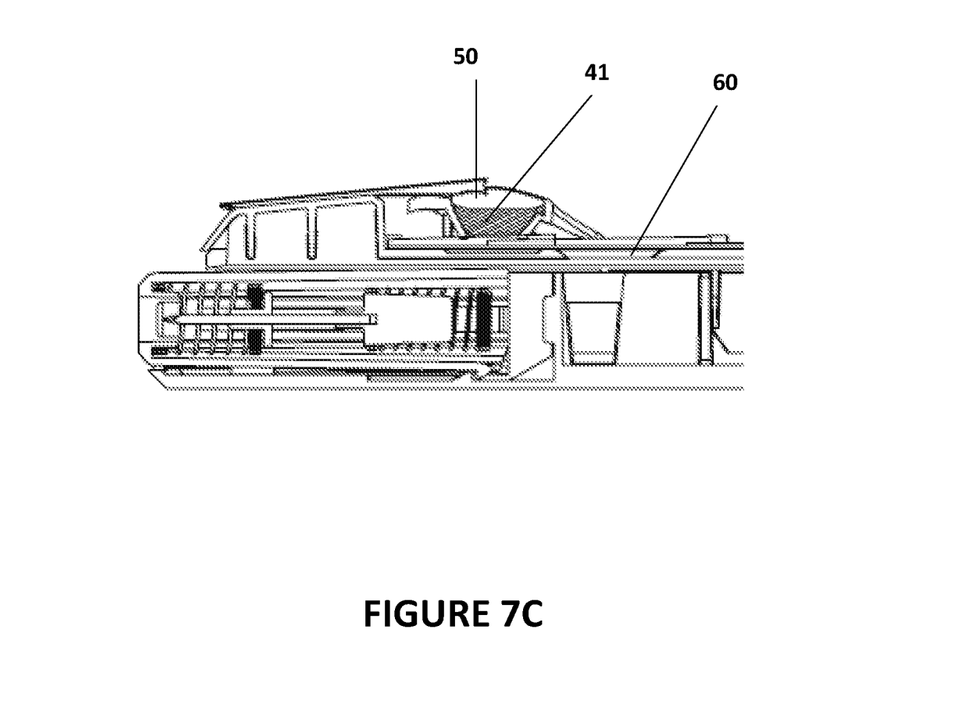

FIGS. 7A, 7B and 7C illustrate in more detail the sequence of test fluid discharge in the illustrative device. In FIG. 7A, the sachet 40 contains the test fluid 41 and has yet to be discharged by pressure from depressible portion 26. It can be seen that some of the fluid 41 is also in the tube section 44.

In FIG. 7B, depressible portion 26 has been depressed, and test fluid 41 has been discharged (as illustrated by the arrow) into vessel 50. Vessel 50 is more or less directly engaged with test material 60. It will be appreciated that in other implementations, different fluid flow paths and geometry could be employed.

In FIG. 7C, the test fluid 41 is discharging in a controlled way through opening 51 (not visible in this view) onto test component 60. Thus, test fluid 41 is discharged in a measured, controlled way onto test component 60 and not in an uncontained rush.

It will be understood that while the fluid will discharge over time, it will not necessarily be at a constant rate. The rate will be determined in part by the sizes of the opening (or openings) in the vessel, as well as the absorption by the test material. Flow may slow as more or most of the fluid has left the vessel, for example.

The fluid in the sachet may be any kind of fluid necessary or desired to perform or validate the test. It will be appreciated that the fluid may have different properties, for example density, viscosity and surface tension, and that appropriate changes to the sachet and frangible area may need to be made. The present invention is concerned with how the fluid is delivered, and is applicable to any desired fluid for use with a test.

The test material may be, illustratively, a lateral flow test for a component of blood, electrolyte, blood sugar, cholesterol or any other blood component. It may adapted to detect specific biological or immunological responses, for example the presence of a pathogen or antibodies to a pathogen. Any kind of test on a body fluid which is suitable for this type of test unit can be used. The present invention is not specific to any type or form of test material, whether of lateral flow type or otherwise. Similarly, it is not constrained to blood, but could be applied to tests on any suitable bodily fluid, for example urine, interstitial fluid, faeces, or sputum, whether directly applied to the test unit or after pre-processing.

It will be appreciated that the specific dimensions, shapes and parameters will need to be determined, in part by trial and error, for specific applications. The required volume of fluid will determine the size of the sachet. The properties of the specific fluid, and the required rate of flow will determine the size and nature of the outlets required in the vessel. The surface properties of the interaction between the specific fluid and the materials over which it will flow also need to be considered. For example, in an aqueous fluid, given the relatively high surface tension, smooth shapes are preferred over corners to ensure a smooth flow of the fluid. The detention vessel illustrated is contained wholly within the test unit, however, it will be appreciated that this could be partly open if desired. The required flow rate and volume are specific to the particular test material being used, and will generally be advised by the test material manufacturer.

This implementation accordingly allows for the rate of delivery of a test fluid to be closely controlled. The fluid is first released into the detention vessel. The size, number, and shape of the outlets, as well as the shape of the vessel, will determine the rate (whether variable or constant) at which the fluid is released. For example, if the outlets are relatively small, the fluid will be released over a longer time period. The combination of controlling the volume of the fluid, and its fluid path, allows for relatively accurate control of the delivery of the fluid, and further ensures that it is delivered to the correct point on the test material.

The present invention may be implemented in ways that do not incorporate all of the preferred features noted in relation to the example above. For instance, the sample of blood or other fluid could be placed directly into a suitable recess or opening in the test unit, without using the capillary or another mechanism. The buffer reservoir may not be integrated, but rather could be a separate bottle or sachet. The detention vessel in this instance would include an opening or passage for the entry of the fluid from the external container.

The present invention includes within its scope a device in which all the fluid components—the reservoir, the vessel and any conduits between are integrally formed into a device. However, it is presently preferred, for reasons of practical manufacturing, that the reservoir be separately formed. This facilitates, for example, the sizing of different reservoirs or sachet for different test components, and the replacement during manufacture of these in tandem.

Although a sachet has been described to retain the fluid, it will be appreciated that the present invention is by no means limited to such an arrangement. The sachet could be formed, for example, as a blister pack type unit, in a foil container, or in any other suitable way. The reservoir could be simply formed in the test unit, and filled during the process of manufacture. Another type of frangible container, which will open at a selected point under pressure or other stimulus, could be used. More than one fluid could be provided, either to be delivered at once, or sequentially, or in the alternative.

Figure 8A:
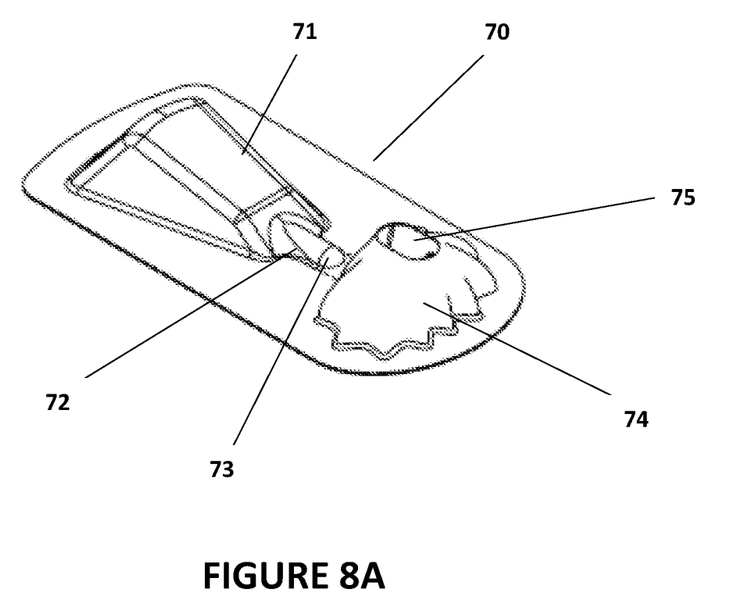
FIGS. 8A and 8B illustrate an alternative reservoir with integral discharge vessel.

FIGS. 8A and 8B illustrate an implementation in which the vessel is provided as part of the sachet unit. Unit 70 includes a reservoir 71, tube 72 and seal 73 similar to those in FIG. 6A. However, vessel 75 is also provided as part of the blister type structure, with an opening 74. It will be appreciated that this is shown upside down for illustrative purposes.

Figure 8B:
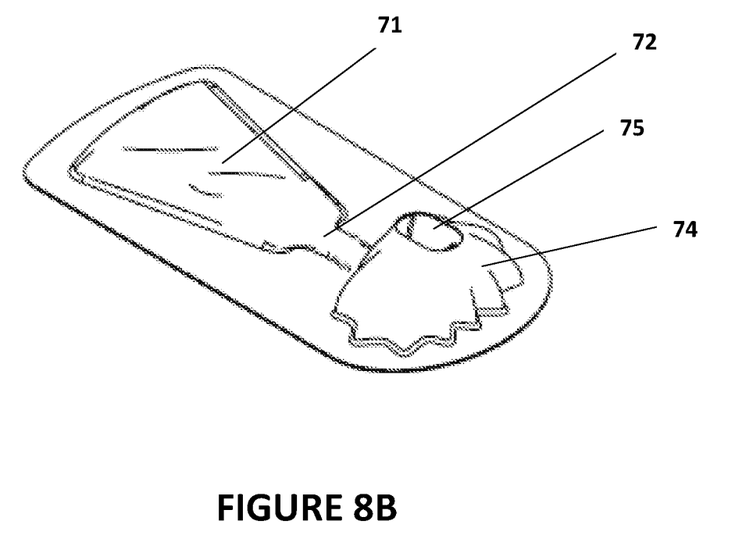

Once the sachet is depressed, as shown in FIG. 8B, seal 73 fails and the test fluid passes into the vessel 75, where in operation it discharges in a controlled way onto the test material (not shown in this view). In this case, the test unit would not include an integrated reservoir, but rather have an appropriate recess for unit 70 under the depressible portion 26, so that opening 75 discharged directly onto the test component 60.

It will be understood that the illustrative embodiments are only provided by way of example, and many other structures could be used to implement the invention, and in particular, the control vessel. These implementations will be necessarily varied in form and mechanism dependent upon the test system in which they are to be employed.

The invention claimed is:

1. An integrated testing device comprising:
a test component;
a reservoir; and
a fluid delivery actuator;
the device further including a control vessel, and in operation the fluid delivery actuator causes a test fluid to be released from the reservoir into the control vessel,
wherein the control vessel comprising one or more openings in its bottom wall and being positioned above the test component so as to provide a controlled volume discharge of test fluid directly onto the test component via the one or more openings.

2. An integrated testing device according to claim 1, wherein the control vessel is integrally formed with said device, and the reservoir and test component are formed separately.

3. An integrated testing device according to claim 1, wherein the control vessel and the reservoir are formed together as a separate component.

4. A testing device according to claim 3, wherein the reservoir and the control vessel are connected by a tube.

5. An integrated testing device according to claim 1, wherein the device further includes an interlock assembly so that operation of the interlock assembly causes the fluid delivery actuator to be inoperable until after a sample is delivered to the test component.

6. An integrated testing device according to claim 1, wherein the controlled volume discharge is controlled by the shape and disposition of one or more selected from the group consisting of the reservoir, the control vessel, the openings in the control vessel, and the fluid paths between and therefrom.

7. A testing device including a control vessel, and a test component, a test fluid being released from a separate or integral reservoir into the control vessel, the control vessel comprising one or more openings in its bottom wall and being positioned above the test component so as to provide a controlled volume discharge of test fluid directly onto the test component via one or more openings.

8. A testing device according to claim 7, wherein the device further includes an interlock assembly so that operation of the interlock assembly causes a fluid delivery actuator to be inoperable until after a sample is delivered to the test component, and the test fluid is discharged after the sample is delivered, such that the controlled volume discharge of test fluid reaches the test component after the sample is delivered to the test component.

9. A testing device according to claim 7, wherein the controlled volume discharge is controlled by the shape and disposition of one or more selected from the group consisting of the reservoir, the control vessel, the openings in the control vessel, and the fluid paths between and therefrom.

10. A testing device according to claim 7, wherein the control vessel and the reservoir are formed together as a separate component.

11. A testing device according to claim 10, wherein the reservoir and the control vessel are connected by a tube.

12. A testing device according to claim 7, wherein the control vessel is integrally formed with said device, and the reservoir and test component are formed separately.

* * * * *